United States Patent
Peeters et al.

(12) Patent No.: US 6,355,064 B1
(45) Date of Patent: Mar. 12, 2002

(54) IMPLANTED HEARING PROSTHESIS

(76) Inventors: Stefaan Peeters, Kleistraat 135, 2630 Aartselaar; Erwin Offeciers, Kerkstraat 161, 2060 Antwerpen; Nick Van Ruiten, Zonnedauw 30, 2970's Gravenwezel-Schilde, all of (BE)

( * ) Notice: Subject to any disclaimer, the term of this patent is extended or adjusted under 35 U.S.C. 154(b) by 0 days.

(21) Appl. No.: 09/171,329
(22) PCT Filed: Apr. 17, 1997
(86) PCT No.: PCT/BE97/00047
 § 371 Date: Jun. 28, 1999
 § 102(e) Date: Jun. 28, 1999
(87) PCT Pub. No.: WO97/38653
 PCT Pub. Date: Oct. 23, 1997

(30) Foreign Application Priority Data

Apr. 17, 1996 (BE) .............................. 9600334

(51) Int. Cl.[7] .............................. A61F 2/18; A61N 1/36
(52) U.S. Cl. .......................................... 623/10; 607/57
(58) Field of Search ...................... 607/57, 67; 623/10

(56) References Cited

U.S. PATENT DOCUMENTS 4,522,209 A * 6/1985 Patrick et al. ................ 607/57
5,649,970 A * 7/1997 Loeb et al. ................... 607/57
5,876,443 A * 3/1999 Hochmair et al. ............ 607/57
5,922,017 A * 7/1999 Bredberg et al. ............. 607/57

FOREIGN PATENT DOCUMENTS

DE 2823798 9/1979
WO WO9306698 4/1993

* cited by examiner

Primary Examiner—David J. Isabella
(74) Attorney, Agent, or Firm—Gottlieb, Rackman & Reisman, P.C.

(57) ABSTRACT

An auditive prosthesis, including a cochlear implantable electrode-set applied on a carrier. The electrode-set provides electrical currents for stimulating auditory nerves in the modiolus. The electrode-set having a first series of electrode-poles arranged beside each other and at a predetermined distance of each other along a first longitudinal side of the carrier. Each of the electrode-poles of the first set are individually connected with a signal-generator. The signal-generator is a second electrode-pole connected with a signal-generator. The second electrode-pole is arranged along a second longitudinal side of the carrier and extending over substantially the same distance as the first electrode-poles. The signal-generator is provided for generating signals between selected electrode-poles, electrical field-lines with radial and/or longitudinal components.

11 Claims, 3 Drawing Sheets

IMPLANTED HEARING PROSTHESIS

The invention relates to an auditive prosthesis, comprising a cochlear implantable electrode-set applied on a carrier, which electrode-set is provided for applying electrical currents for stimulating auditory nerves in the modiolus, wherein the electrode-set comprises a first series of electrode-poles arranged beside each other and at a distance of each other along a first longitudinal side of the carrier, each of the electrode-poles of said first set are individually connected with a signal-generator, which electrode-set comprises a second electrode-pole connected with the signal-generator, which second electrode-pole is arranged along a second longitudinal side of the carrier.

Such an auditive prosthesis is known from the German patent application 28 23 798. The known prosthesis is implanted in the cochlear of a patient having auditory problems in order to improve his auditory perception. By means of the electrodes, currents are applied, under control of received sound-signals, which currents stimulate the auditory nerves in the modiolus, in order to induce action-potentials in those nerves, which action-potentials will thereafter be transported to the brains for interpretation of the audio-signals. With the known prosthesis the electrode-set is formed of the first and second point-shaped electrode-poles, wherein each electrode-pole is each time connected via a wire with the signal-generator. The second electrode-poles form the earth.

A problem of the known auditive prosthesis is that each electrode-pole has each time to be connected with an individual wire with the signal-generator. In order to obtain an increased spacious resolution of the stimulation-pattern, it is necessary to have a plurality of first poles. In view of the limited space available in the scala tympani, the requirement of each time a wire for each pole leads to a limitation in the number of poles and thus to a limited spacious resolution. By using moreover for the first as well as for the second electrode-poles each time point-shaped electrodes, the geometry of the field-lines to be applied is limited.

It is an object of the invention to realise an auditive prosthesis wherein stimulation with a higher spacious resolution is possible.

An auditive prosthesis according to the invention is therefore characterised in that, the second electrode-pole extends over substantially the same distance as the one over which the first electrode-poles extend and which signal-generator is provided for generating signals which generate between electrode-poles to be selected, electrical field-lines with radial and/or longitudinal components. Due to this the second electrode-pole forms a collective pole and thus only a single wire is necessary for connection with the signal-generator. When the first pole comprises n electrodes only n+1 wires are required, due to which a plurality of first electrode-poles is possible, without having the limited space available in the scala tympani forming too quickly a problem. The combination of the first electrode-poles and the second collective pole offers moreover the possibility to generate by means of the signal-generator signals enabling to generate radial as well as longitudinal field-lines. Using those two kinds of field-lines enables to increase the spacious resolution.

It is favourable that said second pole is longitudinally configured. The configuration of the second electrode-pole thus allies to the one of the carrier.

A first preferred embodiment of an auditive prosthesis according to the invention is characterised in that said signal-generator is provided for generating bi-phase-stimulation-pulses of which a first and second phase have substantially a same time-duration but are opposite to each other. The use of the collective second pole with bi-phase-stimulation enables a better control of the field-lines.

A second preferred embodiment of an auditive prosthesis according to the invention is characterised in that said electrode-set comprises at least one selectable reference-electrode and wherein a feedback-element is applied between the selected reference-electrode and the generator, which feedback-element is provided for reducing to zero the net current measured over a current pulse-period. This enables to avoid direct currents over the electrode-contacts which could be unfavourable for the modiolus.

The invention will now be described more into detail by means of the drawings in which an embodiment of an auditive prosthesis according to the invention is shown. In the drawings.

Figure 3:
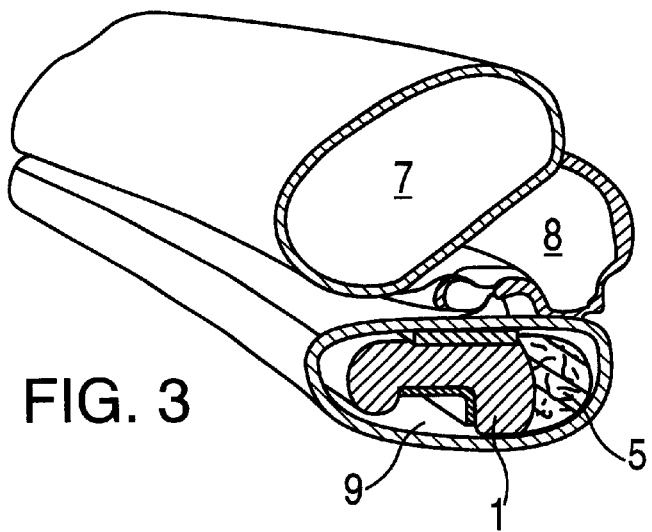
Figure 4:
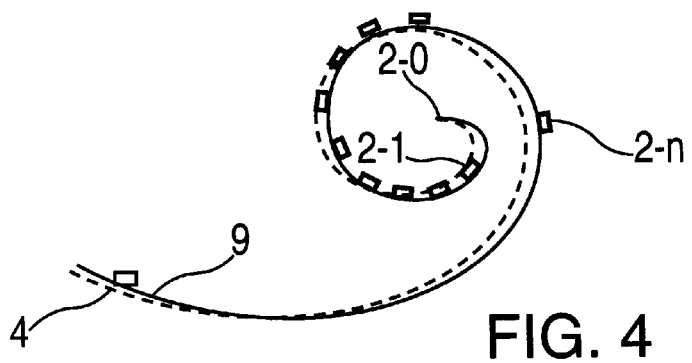
Figure 5:
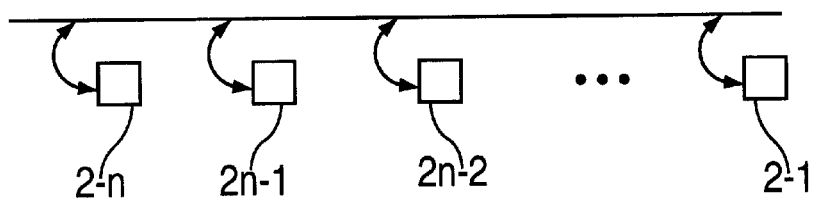
Figure 6:
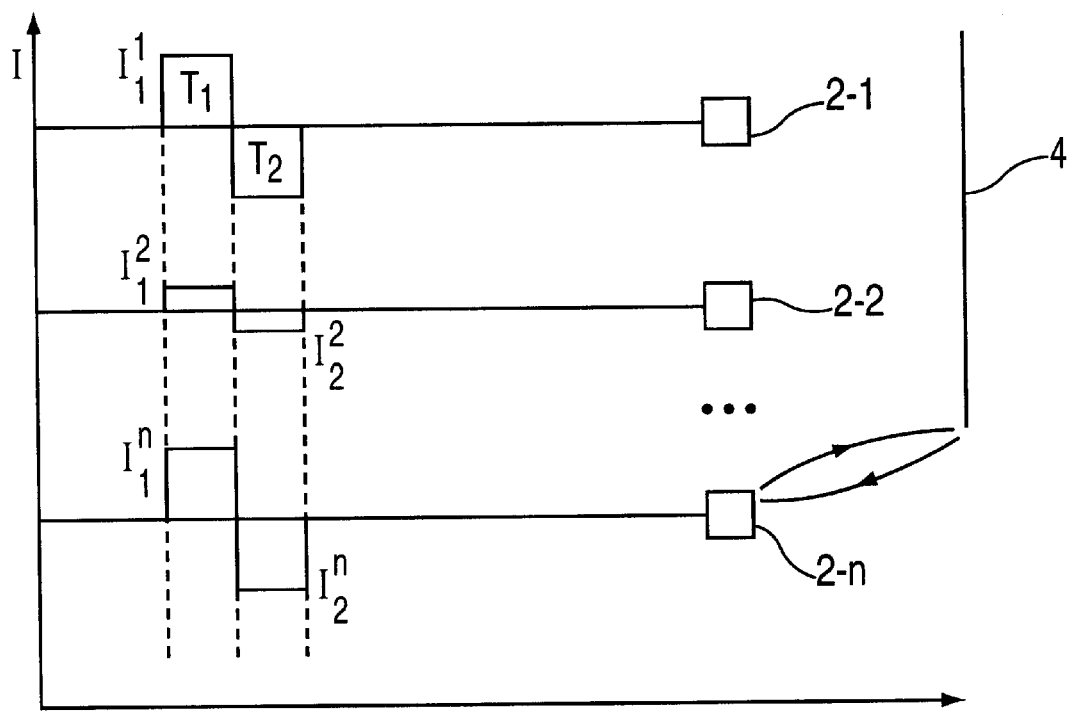
Figure 7:
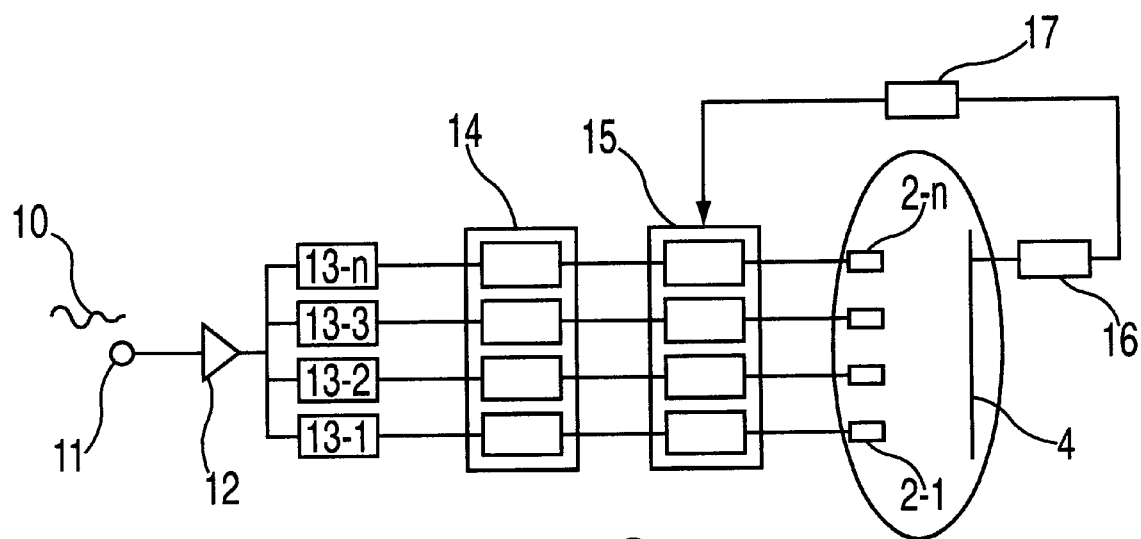
Figure 8:
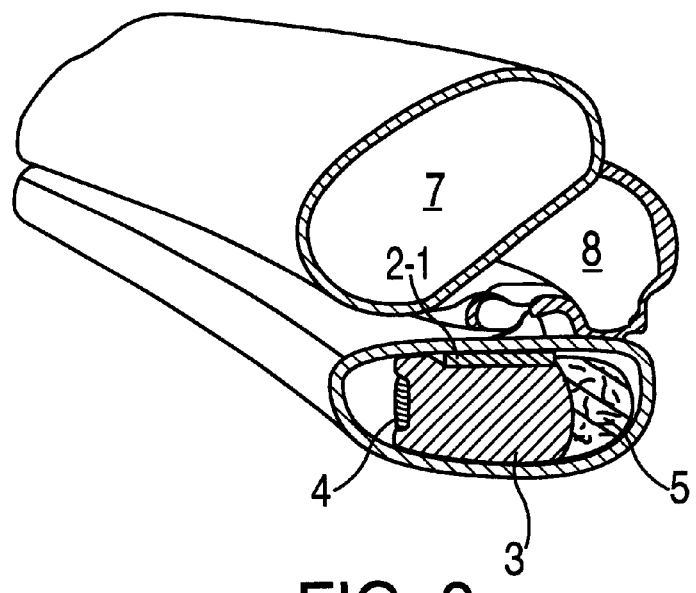

FIG. 3 respectively 8 shows a cross-section of a cochlear of a human ear with a prosthesis according to the invention applied therein;

FIG. 4 and 5 shows schematically the prosthesis according to the invention;

FIG. 6 shows an example of the current-poles-pattern and the electrode-contacts;

FIG. 7 shows a block-scheme of a signal-generator as a component of a prosthesis according to the invention ; and FIG. 8 shows an example of a stimulation-pattern applied to a perception-channel.

In the drawings a same reference sign has been assigned to a same or an analogous element.

Figure 1:
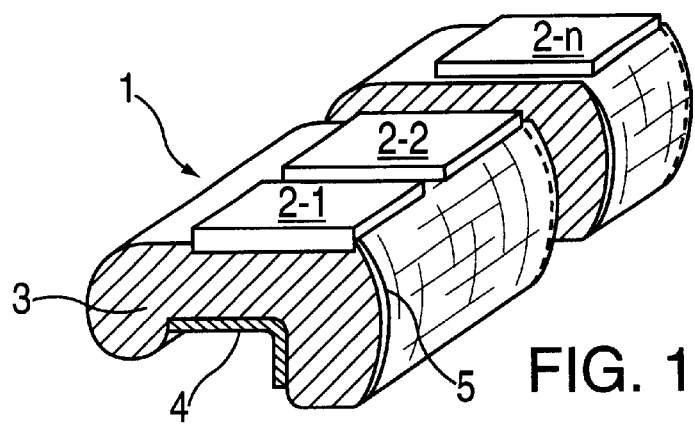
FIG. 1 shows a first embodiment of a carrier provided with electrodes as a part of a prosthesis according to the invention.

The component of an auditive prosthesis according to the invention shown in FIG. 1 comprises a carrier 3 on which at the one longitudinal side a central conductor 4 is applied and at the other opposite longitudinal side a set of n(2-1,2-2, . . . 2-n) for example n=31 electrode-contacts are applied. Those electrode-contacts or electrode-poles are for example formed of Pt or Pt—Ir. The latter are each time applied at a respective distance of one another, for example at 1 mm of each other. The use of a set of electrode-contacts enables it to supply a separate stimulation-pulse per electrode-contact, and in such a manner to stimulate selectively small groups of auditory nerves. The second electrode-pole 4 is built up, either of a single conductor or of a series of individual contacts which are connected to each other. The latter embodiment is advantageous because the prosthesis is more flexible and can thus more easily be applied in the modiolus. The carrier 3 is for example manufactured of silicones enabling him to have a flexible and biocompatible character. The carrier has an electrical resistance of at least 1 Mohm, which is substantially higher than the one of the cochlear liquid, in such a manner that the applied current does not circulate through the carrier.

The carrier 3 preferably has a square profile due to which at the one side a somewhat larger surface is created, on which a swelling member 5 is applied, the function of which will be described later on in this description. Also the central conductor 4 or reference-electrode shows a square profile that joins that of the carrier.

In FIG. 8 a second embodiment of a carrier provided with electrodes is shown. The embodiment shown in that figure distinguishes from the one shown in FIG. 1 by the positioning of the electrodes. The central conductor 4 is now on a lateral side, instead of being at the underside of the carrier 3.

Figure 2:
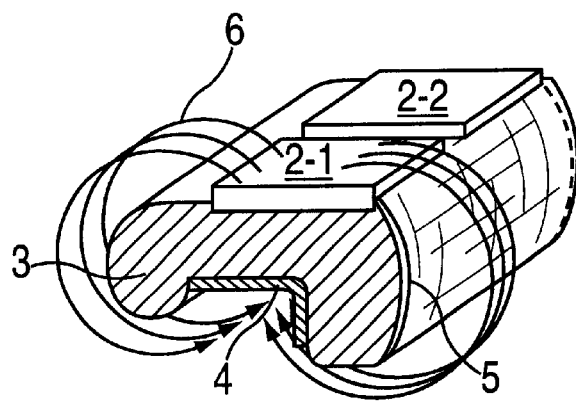
FIG. 2 shows an example of the current-pattern of the electrical field created by the electrodes.

When now current-pulses are supplied to one or more of the electrode-contacts 2-1, 2-2, . . . , 2-n, then currents will flow from the electrode-contacts towards the central conductor 4 and will show a radial pattern as presented in FIG. 2. That radial pattern improves the spacious resolution of the neural stimulation of the nervus acousticus. This moreover corresponds with the direction of the current for which the fibres are the most sensible, due to which the total current-consumption will be reduced.

FIG. 4 illustrates the set-up of an auditive prosthesis according to the invention in a rolled-up configuration. The prosthesis has at one extremity 2-0 a curled configuration, which is pre-formed upon construction.

FIGS. 3 and 8 show a cross-section of the cochlear with the auditive prosthesis according to the invention implanted therein. The cochlear-space comprises a scala vestibuli 7, a scala media 8 and a scala tympani 9. The part of the prosthesis 1 that comprises the electrodes, is applied in the scala tympani. A problem of the known auditive prosthesis is that the electrical conductivity of the liquid, present in the scala tympani, is much higher than the one of the modiolus wherein the auditive nerves are located. Indeed in the modiolus bones are present which have a much larger electrical resistance with respect to the ion-conductivity than the one of the liquid present in the scala tympani. A consequence thereof is that the electrical currents created by the current-pulses will preferably chose a path through the liquid of the scala tympani because it shows a smaller resistance. This leads to an inefficient use of the injected currents.

In order to provide a solution to this problem, a swelling member 5 is preferably applied on the carrier 3, which swelling member is manufactured of a non-electrical conductive material. The function of such a swelling member is for example described in the PCT patent application PCT/AU/92/00517. By filling up that swelling member the dimension of the carrier will increase and will thus take more place in the scala tympani. Due to this, the carrier and the electrodes present thereon, will be pressed against the modiolus. By applying the electrode-contacts in such a manner in the scala tympani, that they are directed towards the scala media 8 and that the central electrode 4 is pressed against the modiolus, the electrode-contacts are pressed against the scala media, due to which the currents will be forced to pass through the modiolus in order to reach the central electrode 4. In such a manner the probability that the current flows through the nerve and will stimulate the latter, is substantially increased and the losses through the conducting liquid in the scala tympani are substantially reduced. Because the carrier now occupies a considerable part of the available space in the scala tympani, it is avoided that the currents will pass through the liquid of the scala tympani. The bad conductivity of the swelling member also contributes to the fact that the current will not preferably chose a path through the swelling member.

The auditive prosthesis according to the invention offers, due to her construction, the possibility to stimulate selectively small groups of nerve-fibres and thus to increase the spacious resolution. Indeed due to the construction of n electrode-contacts, which can be individually stimulated, it is possible to generate a well defined current-pulse for each $i^{th}$ ($1 \leq i \leq n$) electrode-contact of the first electrode-poles, which current-pulse will then apply the suitable stimulus to the nerve in which proximity the electrode-contact is placed. Due to that increased spacious resolution more independent information is sent towards the auditive cortex, due to which the probability of a better speech- understanding by means of the electrical stimulation is increased. The signals supplied to the electrode-poles, are generated by a signal-generator, which is capable of generating a separate signal for each electrode or for a group of electrodes. The central conductor 4 does not necessarily have to be chosen as a minus- or earth-pole. Other configurations wherein one of the first electrode-poles is chosen as a minus- or earth-pole are also possible, wherein then a positive potential is applied to the central conductor. Due to the increased spacious resolution the information, which is stimulated in the nerves, can be better controlled.

Because less current losses arise with the auditive prosthesis according to the invention, the total current-consumption will be reduced, because this is essentially dependent of the necessary currents for stimulating the nerve-fibres. The lower the current, the lower the current-intensities will be on the contact-surface and the smaller the electrode-contacts i-n can be manufactured, without exceeding the safety-norms with which irreversible electrochemical-reactions with the liquid of the scala tympani could arise.

The building-up with n electrode-contacts 2-i and the central-electrode 4, enables to chose one or more reference-electrodes. Due to this the radial as well as the longitudinal component of the current can be influenced. When for example one or more electrodes 2-i together with electrode 4 are selected as reference-electrode and to the other electrodes 2-j ($i \approx j$) a stimulation-pulse is applied, then the longitudinal component will be favoured because the current will flow from 2-j towards 2-i and electrode 4. It is thus possible to select for each stimulation-period another repartition between the different electrodes. The different electrodes can be selected groupswise and per group it is possible to generate a stimulation pattern. Moreover several groups can be simultaneously stimulated. Due to the presence of a plurality of electrodes it is also possible to obtain a larger variation due to which more accurate stimulation between the different electrodes is possible.

In FIG. 5 an example is shown wherein radial field-lines are generated between the first electrodes as well as a longitudinal field-line between the first electrodes 2-n and 2-n-2. According to another example of a stimulation-pattern, a group of 3 electrodes (2-i, 2-i+1 and 2-i+2) is stimulated. In the latter example on electrode 2-i and 2-i+2 a stimulation-pulse with an intensity $-I/2$ is applied in the first half of the period and on electrode 2-i+1 a stimulation-pulse with an intensity I is applied in the first period half. In the second period half the polarity of the current is then reversed. By stimulating groupswise, it is possible to define perception-channels in the cochlear and to assign to each perception-channel a group of first electrodes.

The selectivity, the channel-interaction and the minimalisation of the current-consumption are closely related to each other and determined by the configuration and positioning of the different electrode-contacts with respect to the stimulating part of the nerve-fibres. By pushing the electrode-contacts against the scala media on the one hand and against the modiolus on the other hand, the orientation is optimalised. Due to the choice of n individual stimuli-contacts a configuration is obtained wherein accurately oriented stimulation-pulses can be injected into the nerve.

The generation of stimulation-pulses will now be described by means of the FIGS. 6 and 7. FIG. 6 shows an example of the current-pulses-pattern. In the horizontal direction the time is shown, in the vertical one the current intensity. The currents are bi-phased pulsed and in case of simultaneous radial stimulation all completely in phase. The generated bi-phase current-pulse comprises a first period $T_1$, a second period $T_2$, wherein the current direction in period $T_1$ and $T_2$ is opposite to one another. The duration of period $T_1$ is equal for all n pulses of the n electrode-contacts, in case of simultaneous stimulation as well as for period $T_2$. It is however not necessary that $T_1$ and $T_2$ have the same time duration. By simultaneously applying current-pulses the current-distribution in the cochlear can be better controlled.

The current-amplitude of the first and second phase of the pulse is determined by a preceding processing of the audio-signal. For that purpose the circuit of the transformer 18 shown in FIG. 7, will be described first. The auditive prosthesis comprises a microphone 11, provided to catch an audio-signal 10 and supply it to an amplifier 12. An output of the amplifier 12 is connected with a series of parallelely switched band-pass-filters 13-1, 13-2, ..., 13-n. Those filters divide the audio-signal into n different frequency-ranges. Each $j^{th}$ filter $j(1 \leq j \leq n)$ is connected with a current-transformer 14, which transforms that signal in a current value. That transformation occurs by taking into account the supplied filter-output-values and the pre-selected groups of electrodes, wherein each group each time defines a perception-channel. By using 31 first electrodes there are 31 groups possible. The outputs of the transformer 14 are connected with the inputs of a bi-phase current-pulse-generator 15, which make use of the current value for generating bi-phase-pulses with a period $T_1^j$ and $T_2^j$ with an amplitude $I_1^j$ and $I_2^j$. Each $j^{th}$ electrode-contact is connected with an output of the current-pulse-generator 15. An electrical charge-sensible element 16, such as for example a capacitor, detects the injected net charge over at least one stimulation-period and controls a feedback-element 17, whose output is connected with a control-input of the current-pulse-generator 15.

The received audio-signal is thus processed by the transformer 18, in order to generate in function of that audio-signal simultaneous or continuous interleaved bi-phased current-pulses, which are supplied to the electrode-contacts. The amplitude $I_1^j$ and $I_2^j$ of each $j^{th}$ current-pulse is thus dependent of the supplied audio-signal and channel-wise correlated therewith. With the example shown in FIG. 6, the time-duration $T_1$ of the first phase is equal to the one $T_2$ of the second phase. Also the amplitude $|I_1^j|=|I_2^j|$ for a $j^{th}$ current-pulse. With the stimulation of pre-determined groups of first electrodes, the amplitude of each current-pulse is then determined in function of the stimulation-pattern selected for that group.

In order to avoid direct-currents over the electrode-contacts, which direct-currents could have adverse consequences for the cochlear member, the net current over the total period $T=T_1+T_2$ should be kept at a minimum, and preferably equal to zero. In order to realise the latter the net current for the selected reference-electrode 4 is measured by means of a direct current-meter 16. If the average value over a period T differs from zero then by means of the feedback-element 17 the time-duration of the first and/or second phase will be automatically adjusted or the currents in the first period $T_1$ with respect to the one in the second period $T_2$ (or vice versa) will be adapted in such a manner that the net current averaged over a small period tends towards zero. In such a manner the net direct-current is avoided and it is possible to make no use of individual dissociating-capacitors.

Due to the use of an intra-cochlear-reference-electrode it is possible to individually, radially stimulate. By using pulses in phase, with simultaneous stimulation, it is moreover possible to control better the current-distribution and to provide a feedback-system that avoids the use of disconnecting-capacitors.

What is claimed is:

1. An auditory prosthesis comprising
   a signal generator, and
   a cochlear implantable electrode set provided on a carrier, for applying electrical currents for stimulating auditory nerves in the modiolus;
   wherein the electrode set comprises a first series of electrode poles arranged beside each other and spaced from each other along a first longitudinal side of the carrier, said carrier being arranged and constructed with said first longitudinal side facing the modiolus so that said first series of electrode poles adjacent to the modiolus when implanted; and a single second electrode pole arranged along a second longitudinal side of the carrier and connected to the signal generator, each of the electrode poles of said first set being individually connected to the signal generator; wherein said second electrode pole extends over substantially the same distance as the distance over which the first electrode poles extend;
   and wherein said signal generator generates signals which produce, between electrode poles to be selected, electrical field lines with radial and/or longitudinal components.

2. An auditory prosthesis as claimed in claim 1, characterized in that said second pole is longitudinally configured.

3. An auditory prosthesis as claimed in claim 1, characterized in that said signal generator comprises means for generating bi-phase stimulation pulses, wherein a first and second phase have substantially a same time-duration but are opposite to each other.

4. An auditory prosthesis as claimed in claim 1, characterized in that the first electrode set comprises thirty-one electrodes.

5. An auditory prosthesis as claimed in claim 1, characterized in that the signal generator is provided with a selection element for selecting a group of first electrode poles and for generating groupwise a stimulation pattern.

6. An auditory prosthesis as claimed in claim 1, characterized in that said signal generator comprises means for generating bi-phase stimulation pulses,
   said electrode set comprises at least one selectable reference electrode, and
   the prosthesis further comprises a feedback-element connected between the selected reference-electrode and the generator, for reducing to zero the net current measured over a current-pulse period.

7. An auditory prosthesis as claimed in claim 1, characterized by further comprising a member formed of an electrically non-conducting material, disposed longitudinally along the carrier for filling space within the scala tympani, thereby pressing the electrodes towards the modiolus.

8. An auditory prosthesis as claimed in claim 7, characterized in that said signal generator comprises means for generating bi-phase stimulation pulses,
   said electrode set comprises at least one selectable reference electrode, and
   the prosthesis further comprises a feedback element connected between the selected reference electrode and the generator, for reducing to zero the net current measured over a current-pulse period.

9. An auditory prosthesis comprising
   a signal generator, and a cochlear implantable electrode set provided on a carrier, for applying electrical currents for stimulating auditory nerves in the modiolus, wherein the electrode set comprises a first series of electrode poles arranged beside each other and spaced from each other along a first longitudinal side of the carrier, said carrier being arranged and constructed so that said first londitudinal side is facing the modiolus so that said first series of electrode poles adjacent to the modiolus when implanted; and a single second electrode pole arranged along a second longitudinal side of the carrier and connected to the signal generator, each of the electrode poles of said first set being individually connected to the signal generator; and a member formed of an electrically non-conducting material, disposed longitudinally along the carrier for filling space within the scala tympani to press said first series of the electrode poles towards the modiolus, the second electrode pole extends over substantially the same distance as the distance over which the first electrode poles extend; and wherein said signal generator generates signals which produce, between electrode poles to be selected, electrical field lines with radial and/or longitudinal components.

10. An auditory prosthesis as claimed in claim 9, characterized in that said member is disposed along a side of the carrier opposite to one of the electrodes.

11. An auditory prosthesis as claimed in claim 9, characterized in that said signal generator comprises means for generating bi-phase stimulation pulses, said electrode set comprises at least one selectable reference electrode, and the prosthesis further comprises a feedback element connected between the selected reference electrode and the generator, for reducing to zero the net current measured over a current-pulse period.

* * * * *

UNITED STATES PATENT AND TRADEMARK OFFICE
CERTIFICATE OF CORRECTION

PATENT NO.    : 6,355,064 B1  
DATED         : March 12, 2002  
INVENTOR(S)   : Peeters, Stefan et al.

Page 1 of 1

It is certified that error appears in the above-identified patent and that said Letters Patent is hereby corrected as shown below:

<u>Title page,</u>
Insert the following:

-- [73]  Assignee:  Cochlear Limited
14 Mars Road
Lane Cove, New South Wales 2066
Australia --

Signed and Sealed this

Twenty-seventh Day of May, 2003

JAMES E. ROGAN
*Director of the United States Patent and Trademark Office*